United States Patent
Oostman et al.

(10) Patent No.: US 10,028,802 B2
(45) Date of Patent: Jul. 24, 2018

(54) LOCATOR DEVICE FOR MEDICAL PROCEDURES ON THE BODY SURFACE AND METHOD OF ITS USE

(71) Applicant: Restoration Robotics, Inc., San Jose, CA (US)

(72) Inventors: Zander H. Oostman, Hansville, WA (US); Clifford A. Oostman, Jr., Hansville, WA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 211 days.

(21) Appl. No.: 15/198,394

(22) Filed: Jun. 30, 2016

(65) Prior Publication Data

US 2016/0310230 A1    Oct. 27, 2016

Related U.S. Application Data

(62) Division of application No. 13/831,145, filed on Mar. 14, 2013, now Pat. No. 9,408,691.

(51) Int. Cl.
*A61B 90/00* (2016.01)
*A61F 2/10* (2006.01)
(Continued)

(52) U.S. Cl.
CPC .............. *A61B 90/39* (2016.02); *A61B 34/30* (2016.02); *A61B 90/37* (2016.02); *A61F 2/10* (2013.01); *A61F 2/105* (2013.01); *A61B 2017/00752* (2013.01); *A61B 2034/2065* (2016.02); *A61B 2034/2068* (2016.02);
(Continued)

(58) Field of Classification Search
CPC . A61F 2/10; A61F 2/105; A61B 34/30; A61B 90/37; A61B 90/39; A61B 2017/00752; A61B 2090/3983; A61B 2034/2065; A61B 2090/363;
(Continued)

(56) References Cited

U.S. PATENT DOCUMENTS

| 1,550,403 A | 8/1925 | Turkus |
| 4,370,979 A | 2/1983 | Erickson |

(Continued)

FOREIGN PATENT DOCUMENTS

| DE | 4444130 | 6/1995 |
| WO | WO 2001/003588 | 1/2001 |

(Continued)

OTHER PUBLICATIONS

English Translation of First Office Action dated Jul. 29, 2016 in connection with commonly assigned Chinese Patent Application No. 201480012083.4, (5 pages).

(Continued)

*Primary Examiner* — Christopher L Templeton
*Assistant Examiner* — George J Ulsh

(57) ABSTRACT

Devices and methods are described for performing a procedure on multiple adjacent segments of a body surface. The methods generally involve positioning a locator device on a body surface to delineate a first body surface segment. A first portion of the locator device may be moved while leaving a second portion of the locator device in place as a reference. The second portion of the locator may then be moved to reform the locator device and delineate a second segment of the body surface. Locator devices comprising two detachable portions are also described.

28 Claims, 9 Drawing Sheets

(51) Int. Cl.
    *A61B 34/30*   (2016.01)
    *A61B 17/00*   (2006.01)
    *A61B 34/20*   (2016.01)

(52) U.S. Cl.
    CPC . *A61B 2090/363* (2016.02); *A61B 2090/3937* (2016.02); *A61B 2090/3983* (2016.02); *A61B 2090/3991* (2016.02)

(58) Field of Classification Search
    CPC .... A61B 2090/3937; A61B 2090/3991; A61B 2034/2068
    USPC ........................................................ 606/133
    See application file for complete search history.

(56) References Cited

U.S. PATENT DOCUMENTS

| | | | |
|---|---|---|---|
| 4,434,791 | A | 3/1984 | Darnell |
| 4,621,619 | A | 11/1986 | Sharpe |
| 4,896,680 | A | 1/1990 | Hirshowitz |
| 5,089,009 | A | 2/1992 | Green |
| 5,380,336 | A | 1/1995 | Misko |
| 5,441,540 | A | 8/1995 | Kim |
| 5,449,374 | A | 9/1995 | Dunn |
| 5,486,196 | A | 1/1996 | Hirshowitz |
| 5,531,790 | A | 7/1996 | Frechet |
| 5,549,713 | A | 8/1996 | Kim |
| 5,662,714 | A | 9/1997 | Charvin |
| 5,759,193 | A | 6/1998 | Burbank |
| 5,769,783 | A | 6/1998 | Fowler |
| 5,785,649 | A | 7/1998 | Fowler |
| 5,814,067 | A | 9/1998 | Fleischmann |
| 5,931,777 | A | 8/1999 | Sava |
| 5,964,697 | A | 10/1999 | Fowler |
| 5,971,920 | A | 10/1999 | Nagel |
| 5,972,021 | A | 10/1999 | Huttner |
| 6,036,641 | A | 3/2000 | Taylor |
| 6,120,436 | A | 9/2000 | Anderson |
| 6,159,231 | A | 12/2000 | Looney |
| 6,190,312 | B1 | 2/2001 | Fowler |
| 6,254,624 | B1 | 7/2001 | Oddsen |
| 6,445,943 | B1 | 9/2002 | Ferre |
| 6,464,634 | B1 | 10/2002 | Fraser |
| 6,585,746 | B2 | 7/2003 | Gildenberg |
| 6,695,868 | B2 | 2/2004 | Looney |
| 6,973,202 | B2 | 12/2005 | Mostafavi |
| 7,127,081 | B1 | 10/2006 | Erdem |
| 7,208,006 | B2 | 4/2007 | Fleischmann |
| 7,894,649 | B2 | 2/2011 | Fu |
| 2003/0120298 | A1 | 6/2003 | Gildenberg |
| 2004/0049206 | A1 | 3/2004 | Rassman |
| 2005/0124988 | A1 | 6/2005 | Terrill-Grisoni |
| 2006/0270909 | A1 | 11/2006 | Davis |
| 2007/0016009 | A1 | 1/2007 | Lakin |
| 2007/0021779 | A1 | 1/2007 | Garvin |
| 2007/0049970 | A1 | 3/2007 | Belef |
| 2007/0078466 | A1 | 4/2007 | Bodduluri |
| 2007/0282374 | A1 | 12/2007 | Sogard |
| 2007/0287910 | A1 | 12/2007 | Stallings |
| 2008/0002809 | A1 | 1/2008 | Bodduluri |
| 2008/0027484 | A1 | 1/2008 | Lee |
| 2008/0114395 | A1 | 5/2008 | Mathisen |
| 2008/0202200 | A1 | 8/2008 | West |
| 2010/0030260 | A1 | 2/2010 | Fleischmann |
| 2010/0080415 | A1 | 4/2010 | Qureshi |
| 2010/0166323 | A1 | 7/2010 | Zhao |
| 2010/0191253 | A1 | 7/2010 | Oostman |
| 2011/0077695 | A1 | 3/2011 | Russell |
| 2011/0098722 | A1 | 4/2011 | Ulfarsson |
| 2011/0152627 | A1 | 6/2011 | Tannoury |
| 2011/0178533 | A1 | 7/2011 | Oostman |
| 2012/0158019 | A1 | 6/2012 | Tenney |
| 2014/0074115 | A1 | 3/2014 | Oostman |

FOREIGN PATENT DOCUMENTS

| | | |
|---|---|---|
| WO | WO 2006/132256 | 12/2006 |
| WO | WO 2008/107110 | 9/2008 |
| WO | WO 2008/156838 | 12/2008 |
| WO | WO 2009/155325 | 12/2009 |

OTHER PUBLICATIONS

English Translation of Office Action dated Jun. 28, 2016, in connection with commonly assigned Korean Patent Application No. 10-2015-7023437, (9 pages).

European Search Report and European Search Opinion dated May 3, 2016, in connection with commonly assigned European Patent Application No. 14773919.7, (9 pages).

Office Action dated Apr. 28, 2016, in connection with commonly assigned Australian Patent Application No. 2014242178, (3 pages).

PCT Search and Written Opinion on connection with commonly assigned International Application No. PCT/US14/17514, Applicant Restoration Robotics, Inc., dated Feb. 19, 21015, (12 pages).

English Translation of Second Office Action dated Mar. 31, 2017, in connection with Chinese Patent Application No. 201480012083.4, 1 page.

LOCATOR DEVICE FOR MEDICAL PROCEDURES ON THE BODY SURFACE AND METHOD OF ITS USE

RELATED APPLICATION DATA

The present application is a divisional of co-pending U.S. application Ser. No. 13/831,145 filed Mar. 14, 2013 entitled "Locator Device for Medical Procedures on the Body Surface and Method of Its Use".

TECHNICAL FIELD

The present invention relates generally to medical devices and methods. More specifically, the invention relates to devices and methods, including those for delineating portions of a body surface during a procedure, creating tension on the body surface during procedure and/or providing fiducials in image-guided procedures.

BACKGROUND

There are numerous surgical, cosmetic, therapeutic and dermatological procedures that involve precise placement of medical instruments on a body surface and/or the need to repeat a procedure multiple times at various locations on a body surface. Hair transplantation surgery is one example of such procedures, and it typically involves harvesting donor hair grafts from "donor areas," and implanting them in one or more bald areas ("recipient areas"). Hair transplantation surgery is a very labor-intensive and complex procedure that requires great skill and precision. When performed completely manually, hair transplantation surgery typically requires multiple, lengthy surgical procedures performed over time. As such, the assignee of the present application has developed an image-guided system for harvesting follicular units from a body surface, as described for example in U.S. Patent Publication Number 2007/0106306, which is hereby incorporated by reference. Image guidance is often used to direct movement of automated systems, such as a system for harvesting and implanting follicular units and/or performing other procedures on the skin or other body surfaces. One example of an image-guided, automated method and system is described in U.S. Patent Publication Number 2012/0158019, which is hereby incorporated by reference.

In performing a procedure on a body surface of a patient, it is often necessary or desirable to perform the procedure on multiple portions of the body surface, with each subsequent portion located immediately adjacent to the prior portion so that there are no gaps between, or overlap of, the multiple body surface portions. In other procedures, it may be desirable to have specific and/or consistent amounts of gaps or overlaps between the multiple body surface portions. Also, using some automated systems, such as those described in reference to certain embodiments of the above-referenced patent applications, it may also be necessary to use fiducial markers to guide the system to perform the procedure. In any of these cases, it can be challenging performing a procedure on multiple body surface portions located in desired locations relative to one another. Typically, for example, this may involve manually moving measuring devices, manually marking skin surfaces, approximating locations where prior procedures were performed, and the like. It can also be challenging to assure proper, stable and consistent positioning of fiducial markers in a treatment area. Various embodiments described below seek to address at least some of these challenges.

SUMMARY

The various embodiments described herein are directed to devices and methods for performing a procedure on multiple portions of a body surface. Any of a number of different procedures or portions of procedures may be performed, using devices and methods described herein. In some embodiments, the devices and methods may simply facilitate or enhance a procedure. In general, as used herein, the phrase "performing a procedure" is meant to also include facilitating and/or enhancing a procedure and/or performing, facilitating and/or enhancing part of a procedure.

The embodiments described herein may be used to perform a procedure on multiple portions of a body surface, where the portions are adjacent and non-overlapping. Alternatively, the same or other embodiments may be used to perform a procedure on multiple portions of a body surface, where the portions are overlapping, for example, by a uniform, desired amount or where a desired amount of gap is present between the body surface portions. The various embodiments described herein typically make it easier to perform procedures on multiple body surface portions at consistent locations relative to one another, such as immediately adjacent to one another.

According to one aspect, to facilitate a procedure on multiple, typically adjacent and non-overlapping, body surface segments, the devices and methods described herein typically involve a locator device with a first portion and a second portion. When the portions are coupled together, they delineate a body surface segment or area on which the procedure may be performed. The first portion may also be detached (fully or partially) from the second portion and moved to a new location, while the second portion remains stationary on the body surface and acts as a reference. Once the first portion is repositioned on the body surface, the second portion can be moved to rejoin the first portion, thereby delineating a second body surface segment on which the procedure may be performed. This process may be repeated as often as desired to perform a procedure on a desired number of body surface segments or areas.

In some embodiments, the locator device simply acts as a locator (or "positioner") for helping delineate multiple body surface portions for the procedure. Optionally, the locator device may also act as a skin/scalp tensioner. In other embodiments, the locator device may include multiple fiducials (or "fiducial markers") for guiding an image-guided system that performs the procedure. In some embodiments, the locator device may be a skin/scalp tensioner and also include fiducials.

In some embodiments, the locator device may remain in position while a procedure is performed on a delineated body surface portion. In alternative embodiments, the locator device may be used for marking the body surface, the locator may then be moved, and the procedure may be performed on the marked portion of the body surface. In some embodiments, the locator device may include a frame that has a central opening, and the opening delineates the body surface portions. Alternatively, an outer edge or some other feature(s) of the locator device may delineate the body surface portions in other embodiments.

According to one aspect of the present application, a method for performing a procedure on a body surface of a patient is provided. The method comprising: positioning a locator device on the body surface to delineate a first segment of a body surface; performing the procedure on the first segment of the body surface; moving a first portion of the locator device while leaving a second portion of the locator device stationary, the second portion providing a reference to guide movement of the first portion relative to the second portion; and moving the second portion of the locator device to reform the locator device and delineate a second segment of the body surface. In some embodiments, the first portion of the locator device, or the second portion of the locator device or both comprises a free end when delineating a first segment of the body surface. In other embodiments, at least one of the first portion and the second portion of the locator device is moved from first location on the body surface to a second location on the body surface, and the other of the first or the second portion of the location device is moved to reform at the second location.

According to another aspect of the present application, a method for performing a procedure on a body surface of a patient is provided. The method comprising: positioning a locator device on the body surface in a first location to delineate a first body surface segment, wherein the locator device includes a plurality of fiducials; performing the procedure on the first body surface segment, using an image-guided system guided at least in part by the plurality of the fiducials; moving a first portion of the locator device on the body surface while leaving a second portion of the locator device stationary, wherein the second portion of the locator device provides a reference to guide movement of the first portion relative to the second portion; moving the second portion of the locator device to reform the locator device and delineate a second body surface segment.

In one embodiment, for example, the locator device may include at least four fiducial markers disposed on four opposing sides of the locator device such that the markers form a grid pattern on the body surface. In some embodiments, the locator device includes a central opening that delineates the first and second body surface portions. The opening may be square-shaped, and the fiducial markers may be disposed along each side of the square-shaped opening. In one embodiment, for example, at least four fiducial markers are disposed along each side of the opening.

In another embodiment, a method for performing a procedure on a body surface of a patient may involve: performing a procedure on a body surface of a patient, the method comprising: positioning a locator device on the body surface in a first location; performing the procedure on a first segment of the body surface delineated by the locator device; moving a first portion of the locator device a selected distance from a second portion of the locator device to a second location on the body surface while leaving the second portion of the locator device on the body surface in the first location, wherein the selected distance is dictated by one or more features of the locator device; and moving the second portion of the locator device to reform the locator device in the second location and thus delineate a second body surface segment. In some embodiments, the method may also include performing the procedure on the second body surface portion. Optionally, the method may further involve: moving the first portion of the locator device to a third location on the body surface while leaving the second portion of the locator device on the body surface in the second location; moving the second portion of the locator device to reform the locator device in the third location and thus delineate a third body surface portion; and performing the procedure on the third body surface portion.

In various embodiments, the first and second portions of the locator device may be moved relative to one another in any of a number of suitable ways. For example, the first portion may be moved relative to the second portion by rotating, turning around, flipping over, swiveling, pivoting, or lifting and repositioning the first portion of the locator device relative to the second portion of the locator device.

In some embodiments, the body surface may be scalp, and the procedure may involve harvesting a hair graft, making a site for hair implantation or implanting a hair graft. The procedure may include tattooing skin, removing a skin graft, attaching a skin graft, or any other suitable procedure.

In some embodiments, the method further involves disconnecting the first portion of the locator device from the second portion of the locator device before moving the first portion to the second location. In one embodiment, one or both of the first and the second portions of the locator device may comprise a free end, which can be used as a reference feature. In such an embodiment, for example, one end of the first portion of the locator device, when moved to the second location, may abut the free end of the second portion of the locator device. In other words, the previously free end of the second portion acts as a reference for positioning the first portion. In an alternative embodiment, the reference feature of the locator device may comprise at least one connector, connecting the first portion with the second portion, such that the first portion can only be moved the selected distance from the second portion due to the at least one connector.

In some embodiments, the method may also involve attaching the locator device to the body surface, such as skin, in the first and second locations such that the locator device is immobile relative to the body surface. For example, attaching the frame to the body surface may include adhering the frame to the skin using at least one of adhesive, pins, hooks, barbs or needles.

In another aspect of the application, a device for facilitating a procedure on a body surface of a patient is provided. The device comprising: a frame configured to delineate a segment of the body surface on which the procedure is performed, the frame comprising; a first portion; a second portion operatively connected to, and at least partially detachable from, the first portion; a coupling member on at least one of the first and second portions configured to allow the first and second portions to connect detachably to one another; a bottom surface; and a top surface; and at least one reference feature on or connected to at least one of the first portion or the second portion of the frame so that the first and second portions of the frame can be moved to different locations on the body surface to delineate multiple segments of the body surface.

In some embodiments, the frame may be at least partially flexible to conform to the body surface of the patient. In some embodiments, the frame may include a central opening, where the central opening delineates a segment of the body surface where the procedure is performed through the opening with the frame in place on the body surface.

In some embodiments, the at least one reference feature may include an edge of the first portion of the frame and a corresponding edge of the second portion of the frame, such that when the first portion is moved from a first location on the body surface to a second location, the edge of the first portion is made to abut the corresponding edge of the second portion. In another embodiment, the at least one reference feature may include at least one connector configured to connect the first portion of the frame to the second portion while the first portion is being moved relative to the second portion. For example, in one embodiment, the at least one connector includes two hinges on opposite sides of the first and second portions.

As mentioned above, in some embodiments, the device may include at least three fiducial markers attached to the top surface and/or the bottom surface of the frame and configured to guide an image-guided system to perform at least part of the procedure. For example, in one embodiment, the procedure may be performed at least in part by a robotic hair transplantation system, and the fiducial markers guide the robotic system in performing the procedure. In some embodiments, the frame includes at least four fiducial markers disposed on four opposing sides of the frame such that the markers form a grid. In some embodiments, the frame may include a central opening shaped as a square or rectangle, and the fiducial markers may be disposed along each side of the opening. In some embodiments, at least four fiducial markers are disposed along each side of the opening.

In some embodiments, the frame also acts as a skin tensioner. The frame may include at least one skin adhering member coupled with the bottom surface of the frame. For example, the at least one skin adhering member may include an adhesive, pins, hooks, barbs and/or needles. The device may also include at least two attachment members, where at least one of the attachment members is coupled with each of the first and second portions of the frame to help attach the first and second portions to at least one of the patient or a chair or table on which the patient is sitting or lying.

According to another aspect of the application, a device for facilitating a procedure on a body surface of a patient is provided. The device comprising: a frame forming an opening for delineating a segment of the body surface on which the procedure is performed, the frame comprising; a first portion; a second portion connected to, and at least partially detachable from, the first portion; and a coupling member on the first and second portions configured to allow the first and second portions to detachably couple with one another; at least one reference feature on or connected to at least one of the first portion or the second portion of the frame so that the first and second portions of the frame can be moved to different locations on the body surface to delineate multiple segments of the body surface; and a plurality of fiducial markers attached to the frame and configured to guide an image-guided system to perform at least part of the procedure.

These and other aspects and embodiments will be described in greater detail below.

DETAILED DESCRIPTION

Figure 1:
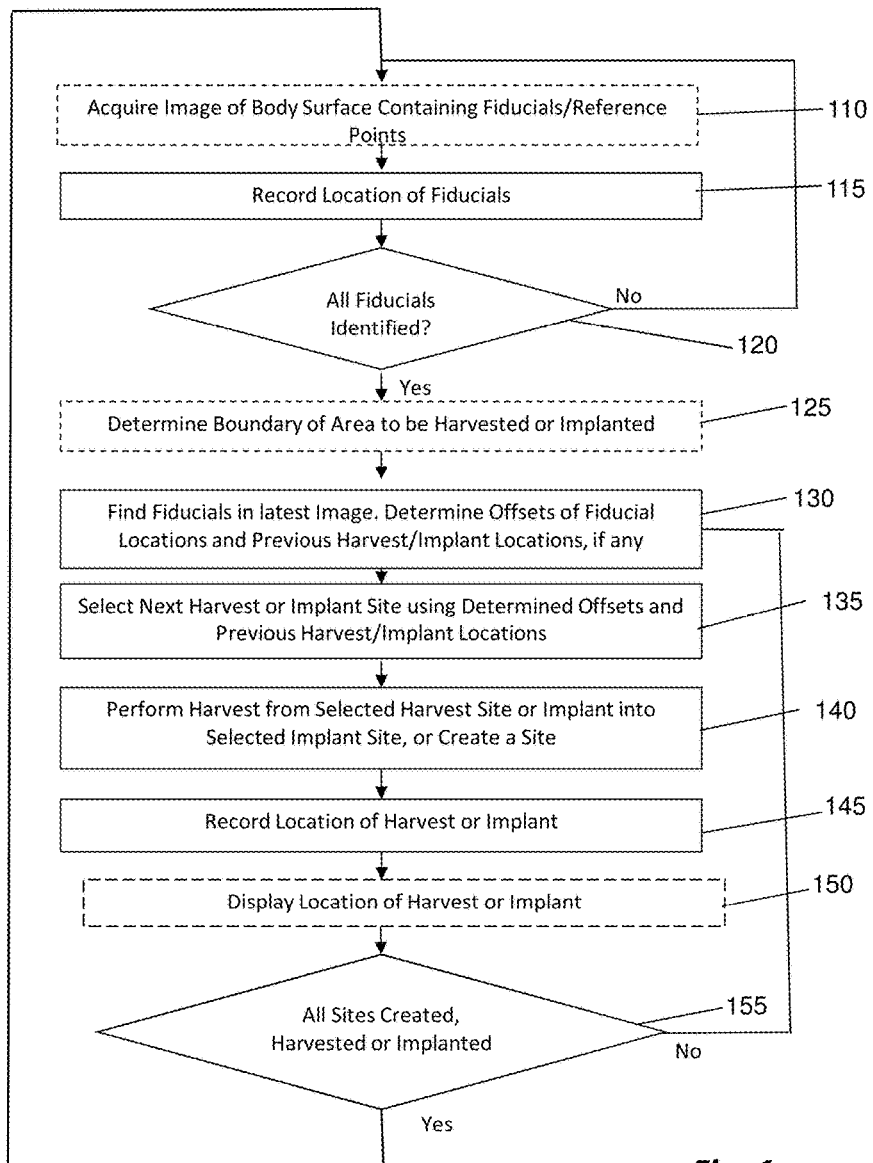
FIG. 1 is a block diagram illustrating one example of a method for performing a hair transplant procedure using fiducials and an image-guided system.

In the following Detailed Description, reference is made to the accompanying drawings that show, by way of illustration, some examples of embodiments in which the invention may be practiced. In this regard, directional terminology, such as "right," "left," "upwards," "downwards," "vertical," "horizontal," etc., are used with reference to the orientation of the Figure(s) being described. Because components or embodiments of the present invention can be positioned or operated in a number of different orientations, the directional terminology is used for purposes of illustration and is in no way limiting. Other embodiments may be used, and structural or logical changes may be made, without departing from the scope of the present invention.

The term "tool," as used herein, refers to any number of tools or end effectors that are capable of performing an action, procedure or operation in various medical procedures or applications. For example, the tool may be a needle, a surgical scalpel, blades, various types of forceps, hemostats, surgical instruments, retractors, electrosurgical tools, radio-frequency ablation tools, suturing devices, tattoo placement or removal tools, cannula, drills or lasers. With reference to hair transplantation procedures, a "tool" may comprise a "harvesting tool" or an "implantation tool," and is capable of dissecting, harvesting or implanting follicular units ("FUs") from or into a skin or body surface, for example, a scalp. Such tools may have many different forms and configurations. In many embodiments, the tool comprises a hollow tubular shaft and thus may be labeled, for example, a cannula, a needle, or a punch. The distal end of such tools (for example, punches, coring devices, cutting and/or trimming devices, needles), are typically sharpened, to various degrees, to penetrate tissue and extract or implant the follicular unit. The terms "operatively connected," "coupled," or "mounted," or "attached" as used herein, means directly or indirectly coupled, attached, or mounted through one or more intervening components.

Embodiments of the methods of the present invention may be implemented using computer software, firmware or hardware. Various programming languages and operating systems may be used to implement the present invention.

Hair transplantation procedures that are carried out using automated (including robotic) systems or computer-controlled systems have been described, for example, in the Publication No. US 2007/0106306 commonly owned by the assignee of the present application, which is incorporated herein by reference. Robotic systems, such as robotic hair transplantation systems generally require accurate positioning of a tool under robotic control. When implementing a semi-automated or a fully automated procedure that requires precise control of the position, such as hair transplantation, it is desirable to be able to maintain such precise control despite patient motion or temporary interruptions.

According to the various embodiments described herein, a variety of devices and methods are provided, which enable a tool (or more generally a procedure) to proceed from where it left off and/or to facilitate performing a procedure (or a portion of a procedure) on multiple portions of adjacent body surface. For example, in reference to hair transplantation, a procedure may be performed manually, semi-automatically or in a fully automated manner, including using image guidance in some embodiments. In any of these cases, when a portion of the procedure is finished on a particular location on the body surface, it may be necessary or desirable precisely and accurately move to a next procedure area where hair grafts will be harvested or implanted, so that there are no gaps between, or overlapping of, the first and second procedure areas. Such gaps may result in under-harvesting or underimplanting, and overlapping may result in overharvesting or overimplanting in the overlapped area. Using currently available methods, it is necessary to manually move fiducials from one location on the scalp to another (in the case of image-guided systems) or to manually estimate where a second procedure location should be placed relative to a first, and so on. This kind of manual movement from one location to another can be very challenging and very dependent upon the skill of the user performing the procedure. Furthermore, factors like bleeding can obscure the procedure area and make the task of moving from one area to the next without gaps or overlaps even more difficult.

The various embodiments described herein seek to alleviate these challenges. The devices and methods described below generally include a locator device that is used for guiding a procedure. The locator device includes two moveable and at least partially detachable portions, such that one of the two portions remains fixed to the body surface while the other of the two portions is being moved and serves as a reference for correct alignment. The devices and methods described herein thus provide self-alignment for performing procedures on multiple segments of skin, scalp or other body surface. Additionally, in some embodiments, the devices may also act as skin tensioners, fiducial carriers, or both.

Although the various examples and embodiments are often described herein with relation to follicular units (naturally occurring aggregates of 1 to 4 hair follicles) or hair grafts, in various alternative embodiments, the various concepts discussed can be applied more broadly to other appropriate applications. Additionally, although the methods described herein are especially suited for use with image-guided systems (including robotic systems) for hair harvesting and/or implanting, they can be applied to other computer-implemented or image-guided applications. For example, devices and methods described herein may be used in various ablation procedures, biopsy procedures, spinal procedures, dermatological procedures (e.g., tattooing or tattoo removal, or treating various dermatological conditions, such as skin cancers) and other procedures that could benefit from the locator device described herein. Therefore, the examples provided herein are for the purposes of illustration and example only, and this description is not intended to be exhaustive or limiting.

FIG. 1 is a block diagram illustrating an example of a methodology of using image guidance and fiducials in performing a procedure on a body surface that could be implemented with the locator device and method of its use according to the present disclosure. At step 110 (which may be a preliminary step and it is shown in dotted line), one or more images of the body surface with one or more reference points, such as a plurality of fiducials, may be obtained, for example, using an image acquisition device. This may be accomplished by any technique known in the art. For example, in some embodiments, an image acquisition device may be attached to a robotic arm, and the robotic arm with the attached image acquisition device may be positioned so that the harvesting or implantation region is in focus for the cameras. In other embodiments, the image acquisition device may be incorporated into the automated (e.g., robotic) system but not attached to the robotic arm. Alternatively, in further embodiments, the image acquisition device could be a device separate from the robotic system.

As used in this application, a "fiducial" (or "fiducial marker") is an object that may act as a reference, and may be identifiable in a field of view of an imaging device. Fiducials can take many forms, for example, a single artificial reference point that uniquely identifies both position and orientation may be used as a fiducial. Take for example, a set of coordinate axes printed on a surface. A set of reference points that each uniquely specifies a position can be used as fiducials. The combination of three or more such reference points can specify a unique frame of reference specifying both position and orientation. An example would be spheres with different colors. One sphere uniquely specifies a position in space, but not orientation. Two more spheres can be used to specify both position and orientation.

Although dots placed directly on the skin or natural features, such as anatomical landmarks or skin markings, may be used as fiducials in some procedures, they generally will not work in procedures discussed herein. Such fiducials are often obscured by blood and other fluids, may be washed away (in the case of dots marked on skin with a marker, for example). Therefore, various embodiments of a locator device are described herein that include fiducials, to overcome some of the drawbacks associated with natural fiducials and fiducials marked directly on the skin.

At step 115, a processor or an image processor, an example of which is described later in reference to FIG. 2, processes and records an identity and a location of each of the fiducials in a frame of reference of an image acquisition device (e.g., in a camera field of view). Such initial recording of fiducials could be referred to as "fiducial registration." The fiducials could be recorded in various coordinate systems, for example, in a fixed "world" coordinate system. In situations in which an image acquired by the image acquisition device includes only a subset of the fiducials, such that images of additional fiducials are needed, step 120 provides for acquiring additional images as needed, for example, including other subsets of the fiducials, until all fiducials have been identified. In an optional step 125 (shown in dotted line), based on the location of the each of the plurality of fiducials, a boundary of an area, such an area within which hair grafts or follicular units are intended to be harvested from or implanted into, may be determined. The boundaries may be determined automatically, for example, by drawing lines between various fiducials. The boundaries may be also adjusted to eliminate certain portions of the bound area where harvesting or implantation is difficult.

In order to accommodate for patient motion, temporary interruptions, and any other incident that may cause a shift in location of the fiducials in the camera reference frame, as often as required (as may be determined by the user), updated images of the body surface are acquired, the images containing an image of the plurality of fiducials or a subset thereof. Due to patient motion, or another such temporary interruption, the locations of the fiducials in these updated images may be in a revised location with respect to the frame of reference of the image acquisition device.

The processor, in step 130, processes the revised location of each of the plurality of fiducials in the frame of reference of the image acquisition device, the revised locations of each of the plurality of fiducials which may be different from the locations previously processed. Having acquired the revised locations of the fiducials, and with the knowledge of the original locations of the fiducials, an offset for at least some or all of the fiducial locations may be determined in step 130. Based on this offset information, the processor, also in step 130, may process revised locations for each of the locations of interest, such as locations from which follicular units have already been harvested (if harvesting has already started in a region of interest within the boundary) or into which follicular units have already been implanted (if such implanting has been started).

Optionally, step 130 may also comprise determining the revised boundary, for example, of the harvesting/implanting area based on the revised locations of the fiducials. However, it is not necessary, in some embodiments, to determine the whole revised boundary, as this information may be automatically ascertained simply based on the offset of the minimum number of the fiducials. In reference to the example of hair transplantation, having determined the offsets, and with the knowledge of the locations of the follicular units that have been harvested or implanted (if any) with respect of the fiducials, it is possible in step 135 to determine or select a location from where the next hair follicle is to be harvested such that hair follicles are not taken from an already harvested location, or to determine a location into which the next hair follicle is to be implanted such that hair follicles are not implanted into locations into which hair follicles have already been implanted. Such selection may be made using a processor programmed to perform the above-described step, such as a processor described in reference to FIG. 2.

In step 140, a hair graft or follicular unit is harvested from or implanted into the selected location, or a site for implantation is created. When the next hair follicle is harvested or implanted, the location from where it has been harvested from, or implanted into, or where a new site is created, may be registered or recorded by the processor in step 145. This registration may include information on the location of the harvest or implant with respect to at least one of the plurality of fiducials, or the determined boundary.

Optionally, in step 150, the method may comprise creating and displaying a virtual representation on the image of the location from which the follicular unit has been harvested (or at least dissected from the surrounding tissue for further removal using forceps or vacuum), or the location for creating an implantation site, or the location into which a follicular unit has been implanted. Such visual representation, for example, on a monitor (e.g. a computer screen) is especially beneficial for the user to easily and quickly identify locations where hair grafts have been dissected or harvested, and also to differentiate between the previously existing follicular units and the newly implanted ones. The visual representations of step 150 may be implemented by using different colors, shapes or other appropriate differentiating features.

In step 155, the processor determines, based on the information it has recorded with respect to the area and the locations of the follicular units that have been harvested or implanted, if follicular units have been harvested from all desired sites, or if follicular units have been implanted into all desired sites, or if all desired implantation sites have been created. In the event that all follicular units have been harvested or implanted, or all sites have been created, the processor may communicate this information, for example, to the image acquisition device. In addition, the processor may communicate this information to the user, typically providing an indication to the user (via the monitor, voice command, or any other appropriate technique), for example, that step 110 may begin again at a new donor or recipient region.

In the event there are still follicular units to harvest or implant, or sites to create, the processor continues to repeat steps 130-155 until all desired sites are created, or all desired follicular units are harvested or implanted. For example, updated images with the updated fiducial information are processed, offsets determined, the next harvest site or implant site is selected, etc. In this manner, a methodology is provided to enable hair follicles to continue to be harvested from or implanted into a body surface in a continuous and automatic fashion despite potential patient movements and interruptions. The tool is able to be moved to each new harvesting or implantation location with respect to fiducials, the fiducials providing a mechanism of recognizing the location of the harvesting/implanting area on the body surface, despite movement of the patient, or the image acquisition device.

Figure 2:
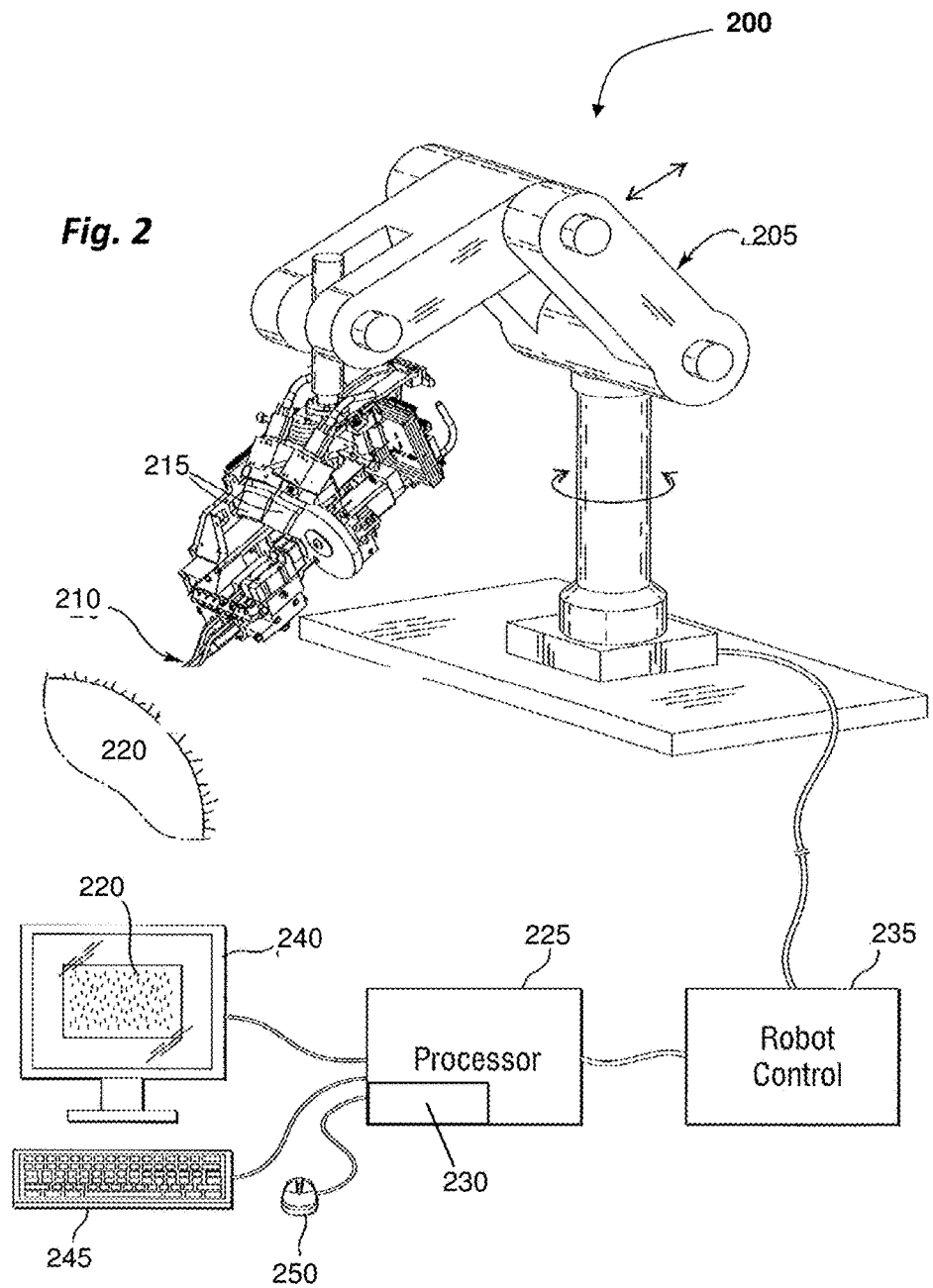
FIG. 2 is a schematic representation of an example of a robotic system that may be used in implementing various embodiments of the present application.

Referring now to FIG. 2, an example of a system that may be used to implement various embodiments of the method described herein is schematically shown. FIG. 2 is a schematic perspective view of an example of a robotic system 200 for hair harvesting (and/or implantation). The system 200 includes a robotic arm 205 to which is coupled a tool 210. Various motors and other movement devices may be incorporated to enable fine movements of an operating tip of the tool 210 in multiple directions. The robotic system 200 further includes at least one image acquisition device 215, which is described in more detail below. The image acquisition device may be mounted in a fixed position, or it may be coupled (directly or indirectly) to a robotic arm 205 or other controllable motion device. The operating tip of the tool 210 is shown positioned over a body surface 220, in this case a part of the patient scalp having hair follicles thereon. In some embodiments, an image acquisition device may be provided separately and not included in the system. In those embodiments, an interface may be provided that allows various other components or modules of the system, such as image processing component, to interact with the separate image acquisition device.

A processor 225 may include an image processor 230 for processing images obtained from the image acquisition device 215. The image processor 230 may be a separate device, or it may be incorporated as a part of the processor 225. The processor 225 may also instruct the various movement devices of the robotic arm 205, including the tool 210 that may be operatively connected to the robotic arm. The processor 225 may act, for example, through a controller 235. The controller 235 may be operatively coupled to the robotic arm and configured to control the motion of the robotic arm, including the motion based on the images or data acquired by the image acquisition device. Alternatively, controller 235 may be incorporated as a part of the processor 225, so that all processing and controls of all movements of all the tools, the robotic arm and any other moveable parts of the assembly, including those based on the images or data acquired by the image acquisition device, are concentrated in one place. The system 200 may further comprise a monitor 240, keyboard 245, and mouse 250. A magnified image of the body surface 220 can be seen on the monitor 240. In addition, the system 200 may include other tools, devices and components, for example, those useful in harvesting, and/or implantation of the hair follicles, or in hair treatment planning. The system further includes an interface adapted to receive an image data, various parts of the system allow an operator to monitor conditions and provide instructions, as needed. The processor 225 may interact with the imaging device 215 via the interface (not shown). The interface may include hardware ports, cables, leads, and other data transmission means, or it may include a computer program.

Some non-limiting examples of the image acquisition device 215 include one or more cameras, such as any commercially available cameras. Of course, various image capture devices (or imaging devices) could be used with any of the embodiments of the systems and methods described herein. For example, the imaging device may be one or more cameras, such as any commercially available cameras. While stereo or multi-view imaging devices are typically very useful in the system 200, it is not necessary to employ such geometries or configurations in all embodiments. Likewise, although it is preferred that the image acquisition device be a digital device, it is not required. For example, the image acquisition device could be an analog TV camera that acquires an initial image, which is then processed into a digital image (for example, via an analog-to-digital device such as a commercial-off-the-shelf frame grabber).

The image acquisition device 215 may be coupled to a processing system, shown incorporated in the processor 225 in FIG. 2, to control the imaging operation and process image data. The processor 225 may comprise any suitable device programmed and configured to perform various methods, including methods directed to automated movement of the hair harvesting/implantation tool to maintain or change a desired direction of travel within a hair donor or hair recipient area. For example, the processor 225 may include a set of instructions for executing operations for: processing one or more images of a body surface to determine locations of a plurality of distinctive fiducials appearing in the one or more images, (in some embodiments, the plurality of the distinctive fiducials may define a boundary); operating a tool to harvest or implant a first follicular unit at a first location; identifying a direction of travel of the tool relative to a body surface based on the first location and on the locations of at least one of the plurality of the distinctive fiducials; causing the tool to travel in the identified direction of travel; and/or operating the tool to harvest or implant a second follicular unit at a second location on the body surface in the direction of travel. The image processor may be programmed and configured to perform various known image processing techniques, for example, segmentation, edge detection, object recognition and selection.

By way of example, and not limitation, a suitable processor or image processor may be a digital processing system that includes one or more processors or other type(s) of device. For example, a processor (image processor) may be a controller or any type of personal computer ("PC"). Alternatively, the processor (image processor) may comprise an Application Specific Integrated Circuit (ASIC) or Field Programmable Gate Array (FPGA). The processor may also include memory, storage devices, and other components generally known in the art (and thus not described in detail herein). The above-described processor could be used in conjunction with various partially automated and fully automated (including robotic) hair transplantation and treatment systems and devices, including but not limited to systems for hair harvesting, or hair transplantation.

The foregoing description, related to FIG. 2, is merely one example of a potential system or apparatus that could be used with the methods and devices discussed in the present application. In alternative embodiments, any other suitable image-guided systems may be used. Moreover, the described methodology may be implemented in manually performed or partially automated procedures. For example, in some embodiments, a user may manually place a locator device on a body surface and, by reconfiguring the locator device as described in more detail below, may precisely identify one or more subsequent areas for performing a relevant procedure.

Figure 3:
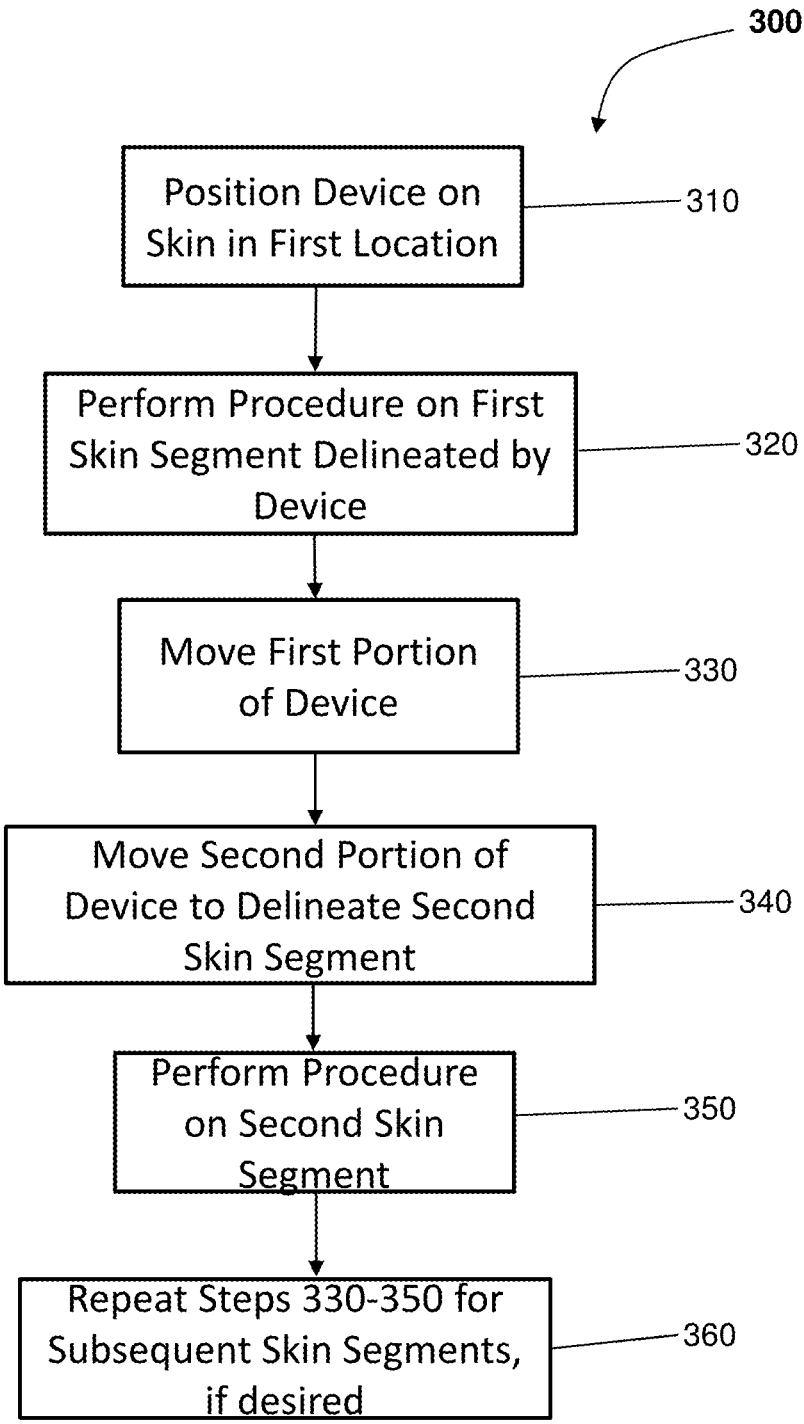
FIG. 3 is a block diagram illustrating a method for performing a procedure (or portion thereof), according to one embodiment.

Referring now to FIG. 3, in a number of embodiments, it may be desirable to perform a procedure sequentially on multiple adjacent overlapping or non-overlapping portions of a body surface, such as skin. With reference to hair transplantation, for example, three procedures that are part of a hair transplantation procedure and that may be performed on multiple sections of the scalp are harvesting (taking donor follicular units), "site-making" (preparing a portion of the scalp for implantation of donor follicular units) and implanting (placing the harvested follicular units into the prepared site(s)). The methods and devices described herein may be applied to any or all of these procedures (or "sub-procedures") in any given embodiment. Additionally, although this description focuses on hair transplantation procedures performed on the scalp, various embodiments may be applied to other skin on other parts of the body and/or for other procedures, such as skin grafting, tattooing and many other procedures. Thus, the description of hair transplantation procedures herein should not be interpreted as limiting the scope of the invention as it is set forth in the claims.

FIG. 3 is a flow chart illustrating one general method 300 of performing a procedure on skin (or another suitable body surface), such as but not limited to a hair transplantation related procedure performed on the scalp. In one embodiment, the method 300 may involve positioning a locator device on skin in a first location (step 310), performing the procedure on a first skin segment delineated by the locator device (step 320), moving a first portion of the locator device (step 330). In various embodiments, the first and the second portions of the locator device may be disconnected from each other, either partially or completely depending on the particular embodiment) prior to movement of the first portion. Also, the movement of the first portion may be accomplished, for example, by simply rotating the first portion (e.g., 180 degrees), by flipping or turning over the first portion from its front side to its back side, by moving the first portion to a different location (e.g., a certain distance away from its previous position), or any combination of the above movements. The above-mentioned examples of the various movements are not intended to be limiting, but rather provided as examples only. In step 340, a second portion of the device may be moved to reconnect with the first portion to delineate a second skin segment. The movement of the second portion may involve various movements, including combination of movements as described in reference to the first portion. Optionally, in step 350 a procedure may be performed on a second skin segment and steps 330-350 may be repeated for one or more subsequent skin segments, if desired (step 360). Generally, while one of the two portions of the locator device is moved, the other portion of the device stays in place, in its first location, on the body surface of the patient. For example, when the first portion is moved, the second portion is used as a reference to show the user or manipulator (for example, a human or a computer-assisted device) where to move the first portion, and the other way around, when the second portion is moved, the first portion stays and may be used as a reference. In this way, the locator device may be used to move across a body surface, sequentially delineating portions of the body surface on which a procedure may be performed.

As will be described further below, in some embodiments, the first and second portions may be attached to one another, such that the first portion may only move a certain distance and/or in a certain direction relative to the second portion. In other embodiments, the second portion may include a reference feature (or features) that mates with one or more reference features of the first portion, so that the first portion can contact the second portion to help the user determine the position.

In various embodiments of the method 300, it may be desirable to move the locator device from the first location to the second location on the skin in such a way that the first and second skin segments are immediately adjacent (or "abutting") one another. As used herein, the phrase "immediately adjacent" means touching but not overlapping. In alternative embodiments, first and second body surface segments may be overlapping by a known, desired amount. In yet other alternative embodiments, first and second body surface segments may be separated by a gap of a known, desired amount. The locator device may be designed, in these various embodiments, with a shape and dimensions to delineate the immediately adjacent, overlapping or gapped body surface segments.

As discussed above, moving a locator device from one body surface segment or area to one or more subsequent, immediately adjacent segments or areas (or consistently overlapping or gapped segments) can be very challenging. In a procedure on the scalp, for example, if a reference device is picked up off of the patient's scalp completely and then repositioned in the second location, it may often be difficult to visualize or determine where the second location is, relative to the first location. For example, if a skin tensioner is picked up by a doctor or other user from a body surface and then placed again in a second location, there may be no reference point on the body of the exact previous location, and the accuracy of the placement will depend solely on the skill and judgment of the doctor or other user. The devices and methods described in the present application address these challenges.

Figure 4A:
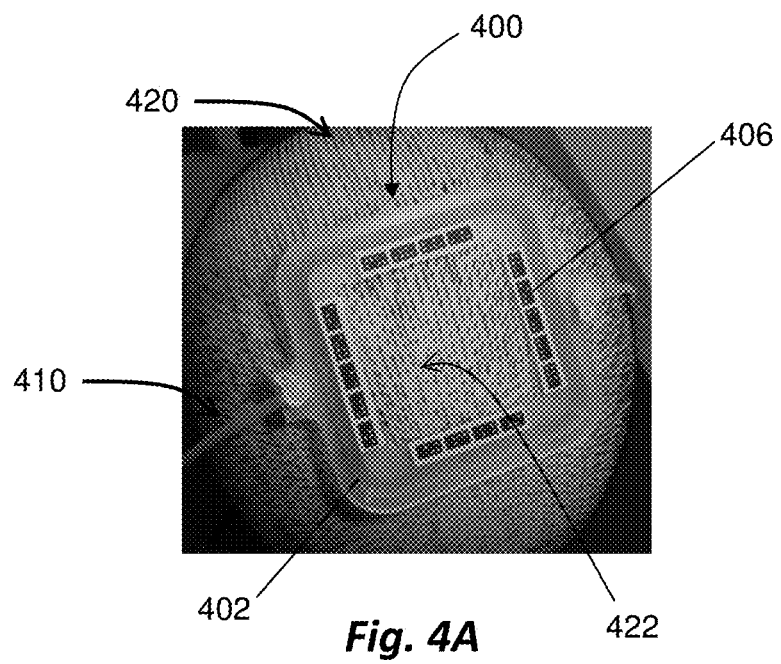
FIGS. 4A and 4B are perspective views of an example of a frame with fiducials.
Figure 4B:
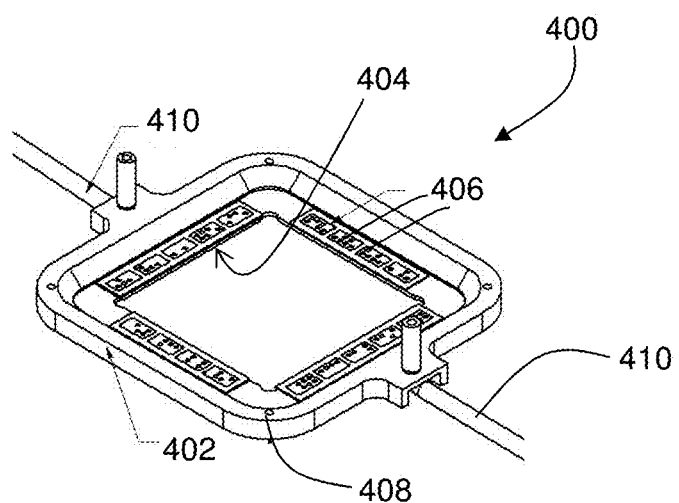

Referring now to FIGS. 4A and 4B, a simplified example of a fiducial-carrying device 400 is illustrated on a model of a scalp 420 (FIG. 4A) and by itself (FIG. 4B). This device 400 is shown for illustrative purposes only. While it does not apply to the method described above in reference to FIG. 3 because it is a one-piece device, it is provided primarily to illustrate, generally, the shape, size and some features of one embodiment of the device 400, which could be adapted with modifications for use in the presently described methods, for example by separating the device 400 into two parts.

In the embodiment shown, the device 400 includes frame 402, with an inner edge 404 that defines a treatment area 422, multiple fiducial markers 406 disposed along the frame 402, pins 408 at the corners of the frame 402 for stabilizing the frame 402 on the scalp, and flexible restraints 410 for attaching the frame 402 to the head or some piece of equipment, such as a procedure chair on which the patient is sitting or lying. In some embodiments, the locator device 400 may also be a skin tensioner, such as but not limited to the skin tensioners described in U.S. Patent Application Pub. No. 2012/0158019, which was previously incorporated by reference, or U.S. Patent Application Pub. No. 2010/0191253, which is hereby incorporated by reference. In the embodiment shown, however, the locator device 400 simply rests on the scalp 420 (or other skin in some embodiments) and serves as a procedure locator and fiducial frame, without tensioning the skin.

The frame 402 may be made of any suitable material and may be any suitable size. In an actual embodiment for use with the presently described method, the frame 402 would be dividable into at least two pieces, so that a first piece could be moved to a different location on the scalp while a second piece could remain stationary and act as a reference for the first piece. The frame 402 may be made of silicone, plastic or rubberized material and may be sized such that the inner edge 404 delineates a treatment area that is small enough to have several treatment areas fit adjacently on a head of a patient. Furthermore, the inner edge 404 may form any suitable shape, such as but not limited to a square, a rectangle, a circle and a triangle. In an alternative embodiments, the frame 402 may be made of flexible or a non-flexible (i.e., rigid) material, may delineate multiple treatment areas simultaneously, and/or the like. The frame 402 may also hold any suitable number of fiducial markers 406, such as between 1 fiducial and 100 fiducials. The embodiment shown includes 18 fiducials 406.

FIGS. 4A and 4B illustrate an embodiment in which a set of unique or distinctive (meaning that they are distinguishable or different from each other) fiducials 406 are either formed on or affixed to the frame 402, which be used in a hair transplant procedure. The frame 402 may lie generally in a plane and may comprise a single element, typically molded material, possibly configured such that it may be compressed inward from a relaxed position. The frame 402, in this embodiment, has four sides arranged substantially in a square, although they may be arcuate and otherwise arranged in various geometrical patterns in alternative embodiments.

In some embodiments, the fiducials 406 may include a single feature, for example a dot, a square, rectangle, a combination of the above, etc.; and each fiducial 406 may be distinguishable from the others by the size of the feature. Alternatively, the fiducials 406 may include a feature (such as a dot, a square, rectangle, a combination of the above, etc.) that may be of the same (or different) size on each fiducial 406, but the fiducials 406 may be further distinguishable from the one another, for example, by the number of the features that it has on it. In further alternative embodiments, each fiducial 406 may comprise a different feature or features. The fiducials 406 can be of any shape or configuration, provided the imaging system is capable of identifying and/or distinguishing them.

Fiducials 406 may be used to assist in image guidance of a device for performing a procedure, for example, a robotic system, such as a follicular unit harvesting or implanting system. In some embodiments, one or more of the fiducials 406 are distinguishable from others. In alternative embodiments, all of the fiducials 406 are distinguishable from each other. The fiducials 406 serve as objects, or reference marks in a field of view of an image acquisition device. These fiducials 406, when viewed in an image, can be recognized in the image, and may be individually recognizable from each other in subsequent images. Fiducials 406 may be physically identified by a 1-D bar code, a 2-D data matrix code, known markings such as alphanumeric characters, a series of dots, a series of bars, or any other type of unique identifier or custom scheme.

Although the embodiment of the device 400 shown in FIGS. 4A and 4B is not usable in its exact form for the methods described herein, any of the features described in reference to FIGS. 4A and 4B, however, may be employed and applied to any of the embodiments of the systems and methods according to the present inventions described further below.

Referring now to FIGS. 5A-5D, one embodiment of a locator device 500 is illustrated, along with a method for using it. In this embodiment, the locator device 500 includes a frame 502 that has two detachable or partially detachable (for example, as described in reference to FIGS. 6-7) pieces or portions—a portion 506 (that may be referred to, for example, as a first portion) and a portion 504 (that may be referred to, for example, as a second portion). Of course, either one of the portions could be a first portion and the other a second portion. The frame 502 may be made of rigid, semi-rigid or flexible material, as discussed above. Each piece 504, 506 may include multiple fiducials 508 attached to its top side, optional flexible attachment members 512, 514 for attaching to a patient's head or a chair or other piece of equipment for stabilization, and coupling members 510, 516 for removably attaching the two portions or pieces 504, 506 to one another. In various alternative embodiments, the coupling members 510, 516 may include hooks, latches, indents, recesses, springs, magnets, pressure fit components, male/female mating features that fit together like puzzle pieces, Velcro, snap fit pieces, or the like. Any type of feature for removably coupling the two pieces 504, 506 may be used. Additionally, in various embodiments, the frame 502 may include more than two pieces 504, 506. Although it may not be necessary and may increase complexity of the device 500, for example, the frame 502 may be divided, for example, into three pieces in one alternative embodiment, where the pieces may be moved from location to location sequentially.

Figure 5A:
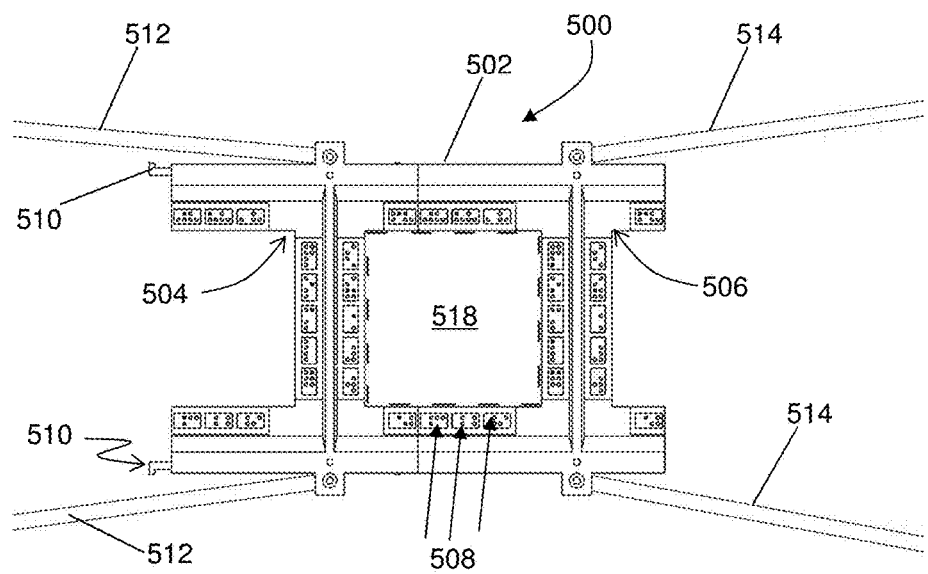
FIGS. 5A-5D are top views of a locator device, according to one embodiment, illustrating a method for moving the locator device from a first location to a second location on a body surface.

Referring first to FIG. 5A, in a first step by way of example, the locator device 500 may be positioned on a patient's skin at a first location to delineate a first scalp segment 518 (or "procedure area") for performing a procedure. A procedure may then be performed on the first scalp segment 518, such as but not limited to tattoo placement, tattoo removal, hair or tissue harvesting, site-making or implanting.

Figure 5B:
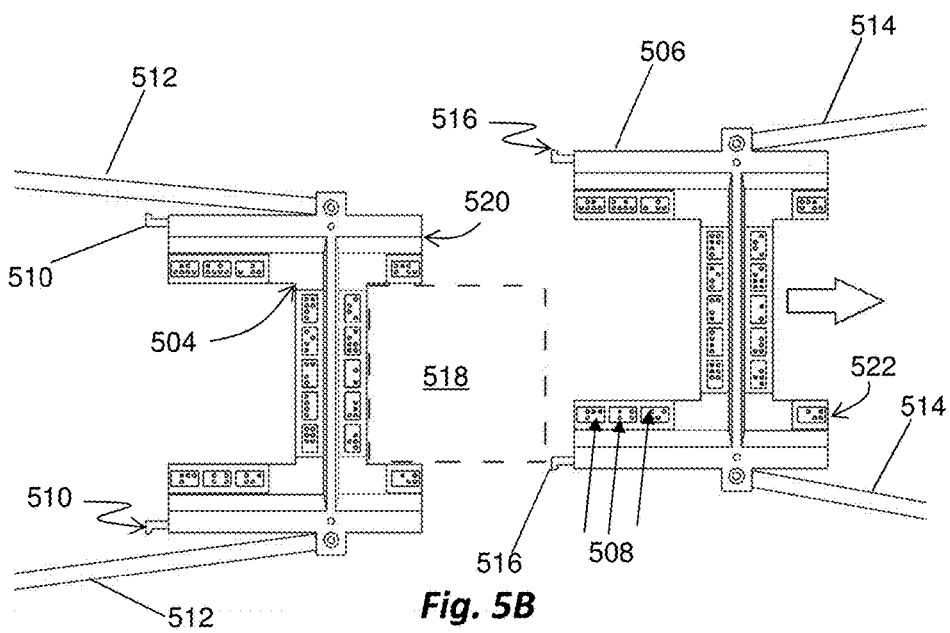

Referring to FIG. 5B, the first piece 506 may then be detached from the second piece 504 of the frame, by detaching the coupling members 516 on the first piece 506 from corresponding coupling members on the second piece 504 (in this embodiment, recessed areas in the frame 502 for hooking onto the coupling members 516). The second piece 504 may be left in place on the patient's skin at this stage, and the first piece 506 may be rotated (or "turned 180 degrees") so that a formerly free end 522 of the first piece 506 abuts a formerly coupled end 520 of the second piece 504.

Figure 5C:
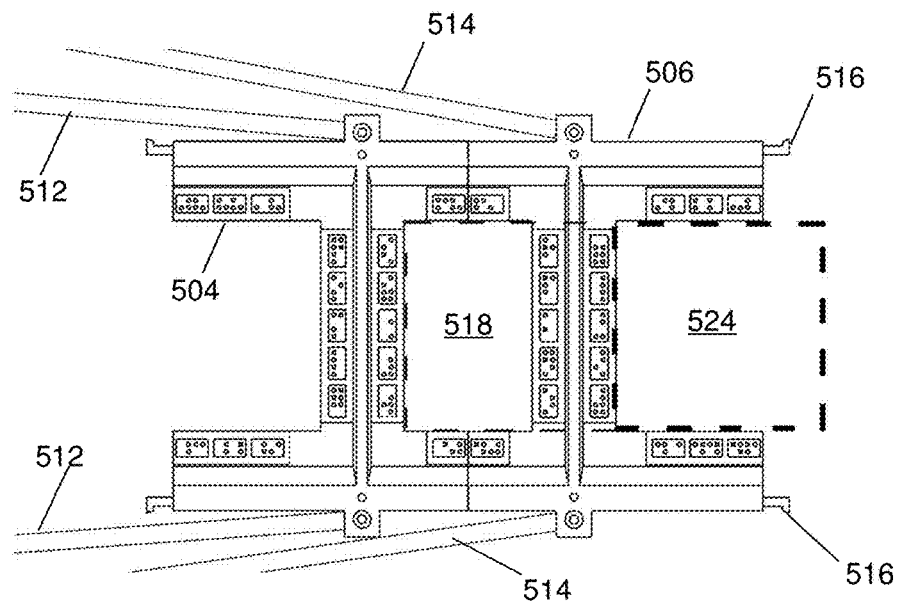

Referring to FIG. 5C, the formerly free end 522 of the first piece 506 now abuts the formerly coupled end 520 of the second piece 504. At this stage, the open end of the first piece 506 has begun to form a second scalp segment 524, which is immediately adjacent the first scalp segment 518. Because the second piece 504 of the frame 502 has not yet been moved, it acts as a registering or locating device for the first piece 506, which thus ensures that one edge of the first scalp segment 518 lines up at least approximately with one edge of the second scalp segment 524. The edges of the first portion and the second portion of the frame may provide reference features, such that when the first portion is moved from a first location on the body surface to a second location, the relevant edge of the first portion is made to abut the corresponding edge of the second portion. Generally, the first piece 506 and the second piece 504 will not be attached at this point but will simply abut one another. In alternative embodiments, if there is an advantage to attaching the two pieces 504, 506, they may be attached at this stage.

Figure 5D:
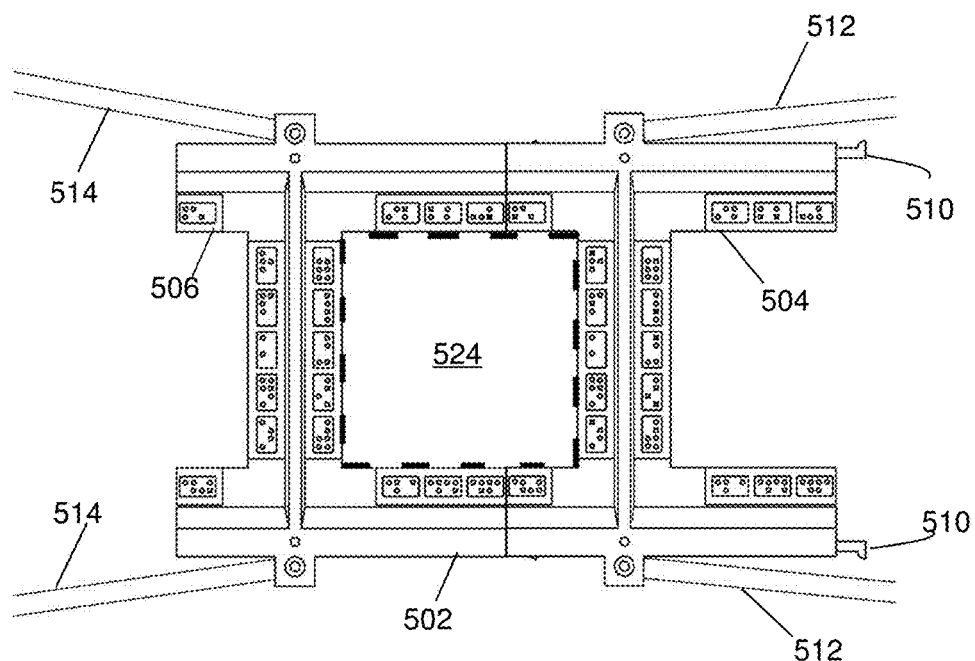

Referring finally to FIG. 5D, the second piece 504 is now rotated (or "turned 180 degrees") around, such that the end 520 is now attached again to the first piece 506 by the coupling members 516. The frame 502 is thus reformed, and the second skin segment 524 is delineated. At this point, the procedure may be performed on the second skin segment 524. This process may be repeated as many times as desired, to perform the procedure on as many skin segments as desired. Again, as illustrated best in FIG. 5C, the successive scalp segments 518, 524 are thus positioned immediately adjacent one another easily and simply, without requiring estimation by a human or machine. In alternative embodiments, the skin segments 518, 524 may be designed to overlap or may be designed with a small gap between them.

The width and the overall size and shape of the frame 502 may be designed such that when the frame is disassembled into the first and second portions 506, 504 and then reassembled at the subsequent body surface location, there will be no overlap between the body surface segments. In particular, the width of the sides of the frame 502 surrounding a central opening may be made proportional to the skin segments 518, 524 (which may be defined by the central opening of the frame), to prevent overlap.

In the embodiment illustrated in FIGS. 5A-5D, the fiducials 508 are located on only one side (referred to as the "top side") of the frame 502. In alternative embodiments, one of which is described below, the fiducials 508 may be positioned on both sides of the frame 502, and the method may involve flipping at least one part of the frame completely over from a "top side" to a "bottom side" during use (described further below in reference to FIGS. 6A-6D). In other alternative embodiments, no fiducials may be included. For example, the frame 502 may simply be used as an outline or guide for a procedure, to demarcate a portion of the body surface, and the procedure may be performed inside the frame 502 by a human user or computer-assisted device. In other embodiments, the frame 502 may be a skin/scalp tensioner but again may not include fiducials. Therefore, although the embodiment described in FIGS. 5A-5D and those described below include fiducials, alternative embodiments may not have fiducials.

In an alternative embodiment, the locator device 500 as illustrated, may utilize a variation of the method described in reference to FIGS. 5A-D to delineate the skin segment. In the alternative method, as above, the locator device 500 may be positioned on a patient's skin at a first location to delineate a first skin segment 518 (or "procedure area") for performing a procedure. However, after detaching the portions 504 and 506 of the frame of the device from each other, the piece or portion 506 may be left in place on the patient's skin at this stage, and the portion 504 may be rotated (or "turned 180 degrees") and moved to the other side of the portion 506 so that a free end of the portion 506 now abuts a formerly coupled end of the portion 504.

At this stage, the coupled end of the second piece 504 has begun to define a more distant edge of a second scalp segment 524, the segment 524 being immediately adjacent the first scalp segment 518. Because the portion 506 of the frame 502 has not yet been moved, it acts as a registering or locating device for the portion 504. Finally, the portion 506 is now rotated in place (or "turned 180 degrees"), such that the end 520 of the portion 504 is now attached again to the portion 506 by the coupling members 516. The frame 502 is thus reformed, and the second scalp segment 524 is delineated. At this point, the procedure may be performed on the second scalp segment 524. As before, this process may be repeated as many times as desired, to perform the procedure on as many scalp portions as desired.

When reference is made to a "procedure" performed on a body surface, this is meant to refer generally to any process performed on a body surface, including a portion of a procedure, a preparation step for a procedure, or a complete procedure. In various alternative embodiments, any of a number of method steps may be substituted, added or deleted from the method described above. For example, in one embodiment, the device 500 may be used to delineate sequential body surface portions, and each new portion may be marked on the body surface, using the device 500 as a guide. After all the portions are marked, the procedure may be performed sequentially on the body surface portions. In one embodiment, for example, the body surface portions may be marked using a tattoo. Alternatively, the portions may be marked using a surgical marker. In some embodiments, the device 500 may not include fiducials, while in other embodiments the device 500 could include fiducials to guide a surgical marking device. In another alternative embodiment where the body surface is marked using the device 500, the marking may be made along the outside edge of the device 500 rather than inside the frame 502. In such an embodiment, for example, the frame 502 might be a solid shape without a central opening.

In some embodiments, flexible attachment members 512, 514 may not be necessary. For example, the frame 502 may adhere to the scalp or other skin surface using barbs, microneedles, adhesive, suction and/or any of a number of adhering members or devices, thus eliminating the need for attachment members 512, 514. In the embodiment shown, the attachment members 512, 514 may attach to a chair or table on which the patient is sitting or lying. Alternatively, the attachment members may attach to the patient or to some other piece of equipment, so long as they assist in keeping the frame 502 stabilized on the patient's head.

Referring now to FIGS. 6A-6D, yet another embodiment of a locator device 600 is illustrated, along with a method of using it. In this embodiment, the locator device 600 again includes a frame 602, having a first portion 604 and a second portion 606, attached to one another with a hinge 608, to delineate a first scalp segment 612 (or "procedure area"). The first portion 604 has a top side 616 with a first set of fiducials 610 attached to it, and the second portion 606 has a top side 618 with a first set of fiducials 613 attached to it. As with the method described previously, initial steps of the method may involve positioning the locator device 600, for example, on the scalp at a desired location to delineate the first scalp segment 612. In this embodiment, the locator device 600 does not include straps to attach the locator device 600 the patient's head or a chair or the like. Instead, the top and bottom sides of the frame 602 may include two or more small pins, hooks, barbs, adhesive, or the like, to attach the frame 602 to the patient's scalp in a relatively stable manner. In alternative embodiments, one or more straps or other attachment devices may be used. It should be understood that small pins, barbs, adhesive, or the like may be used with the embodiments shown in FIGS. 5A-D.

Figure 6A:
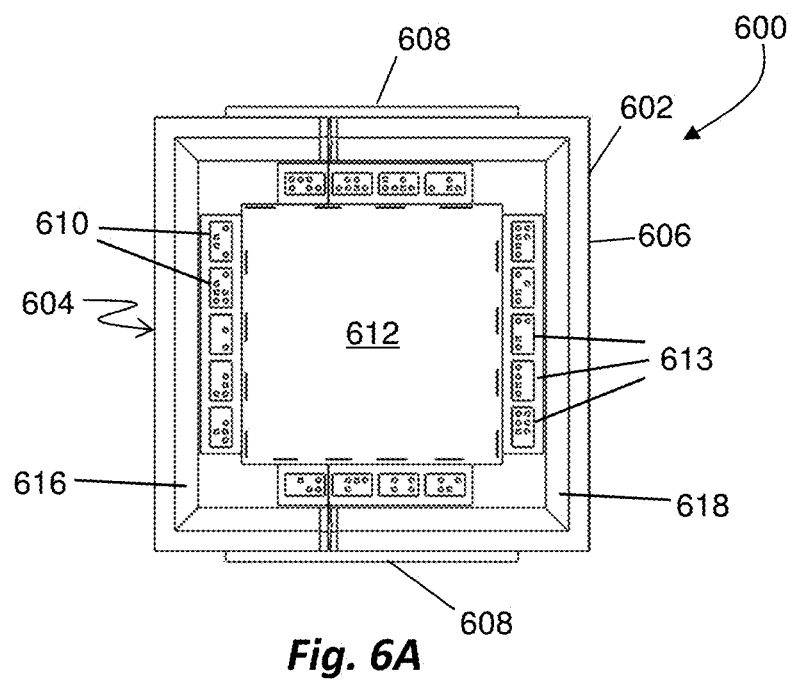
FIGS. 6A-6D are top views of a locator device, according to an alternative embodiment, also illustrating a method for moving the locator device from a first location to a second location on a body surface, according to another alternative embodiment.
Figure 6B:
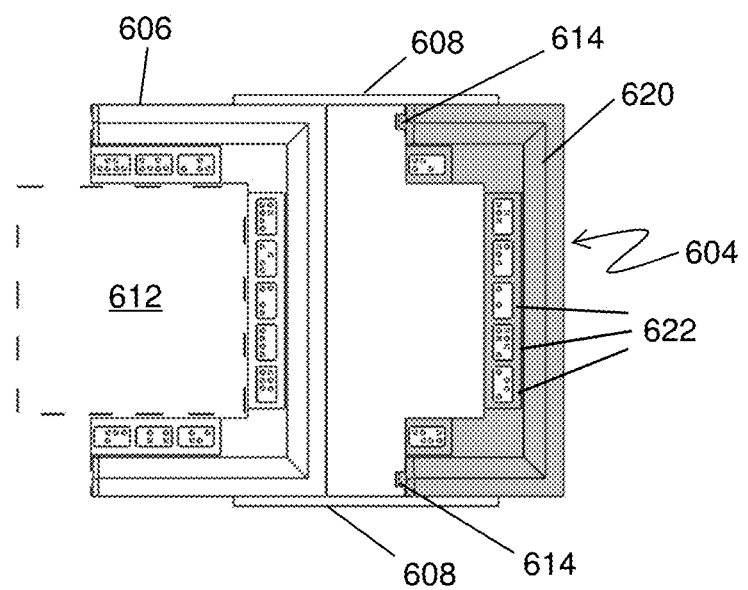

Referring now to FIG. 6B, a second phase of the method may involve detaching the first portion 604 from the second portion 606 and flipping the first portion 604 over the second portion 606 to a new location on the scalp. When flipped over, a bottom side 620 of the first portion 604 is now facing up, along with fiducials 622 attached to the bottom side 620. At this stage, coupling members 614 (optional) on the first portion 604 are exposed. Also at this stage, the first portion 604 may not be directly secured to the scalp in some embodiments, but may simply be secured to the first portion via the hinges 608. Alternatively, the first portion 604 may be secured to the scalp using pins, hooks, needles or the like, located, for example, at each of the two corners of the first portion 604, in one embodiment. In this particular configuration, the hinges 608 additionally provide at least one connector, in the form of a pivot, connecting the first portion with the second portion, such that the first portion can only be moved a selected distance from the second portion due to the at least one connector 608.

Figure 6C:
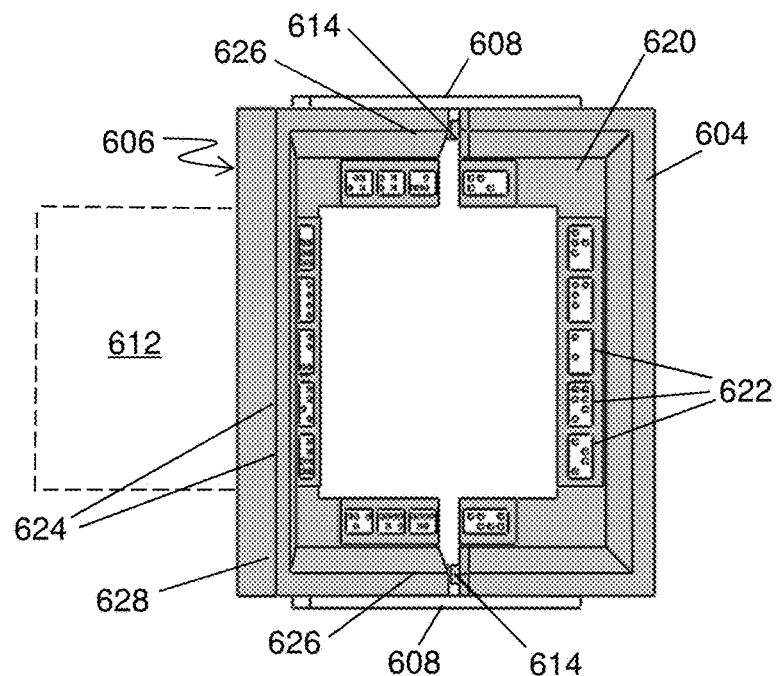

Referring to FIG. 6C, in a next step, the second portion 606 may now be flipped over so that a bottom side 628 and bottom fiducials 624 on the second portion 606 are facing up. The coupling members 614 of the first portion 604 may then be connected with (e.g., inserted into) corresponding coupling members 626 (such as receptacles) of the second portion 606 to reform the frame 602. In some embodiments, the frame 602 may be reformed, and the two portions 604, 606 may be placed together without coupling members 614, 626. In these embodiments, at least one reference feature may include an edge of the first portion of the frame and a corresponding edge of the second portion of the frame, such that when the first portion is moved from a first location on the body surface to a second location, the edge of the first portion is made to abut the corresponding edge of the second portion.

Figure 6D:
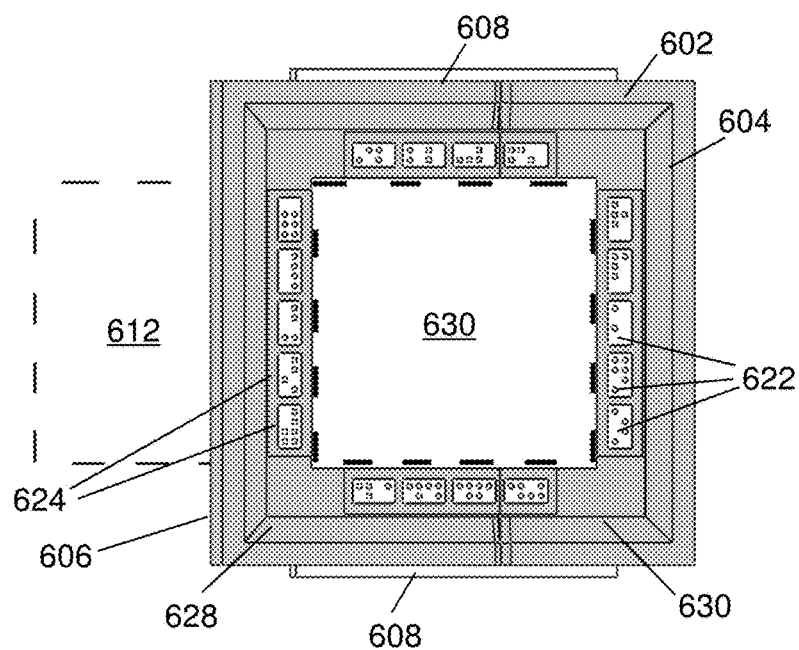

Referring to FIG. 6D, the frame 602 is now reformed in a second location on the scalp, thus delineating a second scalp portion 630, which is immediately adjacent the first scalp portion 612. The frame 602 may be secured to the scalp via pins, hooks, needles or the like, and the procedure may be performed on the second scalp segment 630. These steps may be repeated as many times as desired to cover a desired total area of scalp. As with all of the above-described methods, the fiducials 610, 611, 622, 624 may be used to guide a robotic or computer-automated system to perform the procedure on the various body portions. As also described above, in alternative embodiments, fiducials may not be included.

Figure 7A:
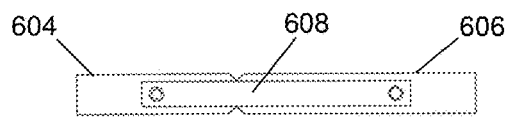
FIGS. 7A-7E are side views of the locator device of FIGS. 6A-6D, illustrating the various steps of the method for moving the locator device, according to one embodiment.
Figure 7B:
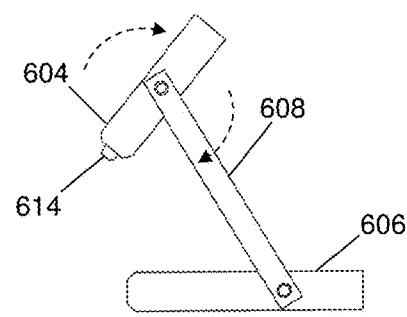
Figure 7C:
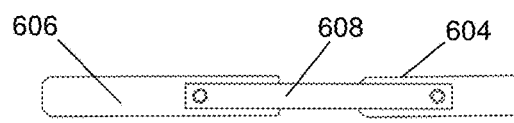

Referring now to FIGS. 7A-7E, a side view illustrates the way in which the first portion 604 and the second portion 606 fit together during the method described above. FIG. 7A shows the first portion 604 and the second portion 606 coupled together in the first body surface location (delineating the first body surface segment). As discussed above, and as illustrated in FIGS. 7B and 7C, the first portion 604 of the locator device 600 may flip over the second portion 606, for example, via the hinge 608, to position the first portion 604 in the new, second location (FIG. 7C). The hinge 608 is sized to position the first portion 604 at a distance from the second portion 606 that will make subsequent body surface portions immediately adjacent one another.

Figure 7D:
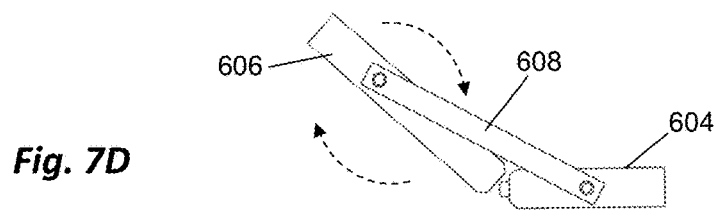
Figure 7E:
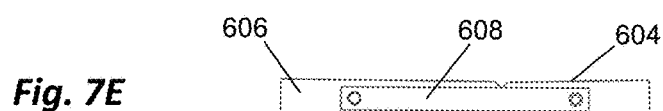

In the next step, as shown in FIG. 7D, the second portion 606 is flipped over on itself (or in place). Finally, as shown in FIG. 7E, the first portion 604 and the second portion 606 are rejoined to reform the frame 602 in the second location and the coupling members 614 may fit into the recesses 626 (or "corresponding coupling members") on the first portion 604. In alternative embodiments, any of a number of alternative connecting structures may be used, such as hooks, pins, détentes, magnets or the like. FIGS. 7A-7E illustrate various stages of the operation of the device according to one embodiment.

Numerous changes, variations, and substitutions will occur to those skilled in the art without departing from the invention. Various alternatives to the embodiments of the invention described herein may be employed in practicing the invention. It should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Similarly, the devices and methods described herein may be used in manual, semi-automated and fully automated procedures, including image-guided and robotic procedures.

What is claimed is:

1. A locator device comprising:
a first portion; and
a second portion operatively connected to, and at least partially detachable from, the first portion,
wherein the first and the second portions have at least one reference feature and, when the at least one reference feature of the first portion abuts the at least one reference feature of the second portion, the first and the second portions form a closed boundary with a central opening, the closed boundary delineating a segment of a body surface on which a procedure is performed; and
wherein a size and configuration of the second portion dictates: 1) movement of the first portion while the second portion remains at its existing location on the body surface and 2) subsequent repositioning of the second portion while the first portion remains in place, such that the at least one reference feature of the first portion and the second portion abut at a new location and the closed boundary delineates a different segment of the body surface.

2. The locator device of claim 1, wherein one or both of moving the first portion and repositioning the second portion comprises rotating or turning around, flipping over or upside down, swiveling, lifting and repositioning, or pivoting.

3. The locator device of claim 1, wherein movement of the first portion while the second portion remains at its existing location comprises rotating or turning around approximately 180 degrees and wherein subsequent repositioning of the second portion comprises rotating or turning around approximately 180 degrees.

4. The locator device of claim 1, wherein the at least one reference feature comprises an edge of the first portion and an edge of the second portion, and the first and the second portions are configured such that the edge of the first portion can be placed to abut the edge of the second portion.

5. The locator device of claim 1, the locator device is configured such that each of the first and the second portions, when remains in place, serves as a reference for the movement of the other of the first and the second portions.

6. The locator device of claim 1, further comprising a top surface and a bottom surface and a plurality of fiducial markers on at least one of the top surface and the bottom surface.

7. The locator device of claim 1, wherein the locator device includes at least four fiducial markers disposed on four opposing sides of the locator device such that the fiducial markers form a grid pattern on the body surface.

8. The locator device of claim 1, wherein the locator device comprises a skin tensioner.

9. The locator device of claim 1, further comprising at least one skin adhering member coupled with or on a bottom surface of the locator device.

10. The locator device of claim 1, further comprising a coupling member on at least one of the first and the second portions configured to allow the first and second portions to connect detachably to each other.

11. The locator device of claim 1, wherein the first and the second portions are connected to each other such that they can only move a certain distance and/or in certain directions relative to each other.

12. The locator device of claim 1, wherein the locator device is configured and has dimensions such that with each move when the at least one reference feature of the first portion and the second portion abut at a new location, the first and the second segments of the body surface are immediately adjacent each other and abut each other.

13. The locator device of claim 1, wherein the locator device is configured and has dimensions such that with each move when the at least one reference feature of the first portion and the second portion abut at a new location, a gap of a same desired amount is formed between the first segment and the second segment, or such that the first and the second segments overlap by a same amount.

14. The locator device of claim 1, wherein the second portion is secured to the first portion via a hinge.

15. A locator device comprising:
a first portion; and
a second portion operatively connected to, and at least partially detachable from, the first portion,
wherein the first and the second portions have mating ends and, when the mating ends abut each other, the first and the second portions form a closed boundary with a central opening, the closed boundary delineating a segment of a body surface on which a procedure is performed; and
wherein the locator device is sized and configured to allow the second portion, while remaining at its existing location on the body surface, dictating a new location where the first portion is movable such that, if one or both of the first and second portions are rotated or turned around, swiveled, or flipped over or upside down, the mating ends of the first and the second portions abut and form the closed boundary which delineates a different segment of the body surface.

16. The locator device of claim 15, wherein the first and the second portions remain at least partially connected to each other at all times, the locator device further comprising at least one connector configured to connect the first portion to the second portion while the first portion is being moved relative to the second portion.

17. The locator device of claim 15, further comprising a top surface and a bottom surface and a plurality of fiducial markers attached to at least one of the top surface or the bottom surface, the plurality of fiducial markers are configured to guide an image-guided system to perform at least part of the procedure.

18. The locator device of claim 15, wherein a bottom surface of the locator device comprises at least one of an adhesive, a pin, a hook, or a barb.

19. The locator device of claim 15, wherein the mating ends comprise an edge of the first portion and an edge of the second portion.

20. The locator device of claim 15, wherein at least one of the first and the second portions is configured to flip over the other and wherein a plurality of fiducials is disposed on both a top and a bottom side of the respective first and second portions.

21. A locator device comprising:
a frame comprising at least two portions operatively connected to, and at least partially detachable from, each other,
wherein each of the at least two portions have at least one reference feature and, when the at least one reference feature of one of the at last two portions abuts the at least one reference feature of the other of the at least two portions, the at least two portions form a closed boundary with at least one central opening, the closed boundary delineating a segment of a body surface on which a procedure is performed; and
wherein a size and configuration of one of the at least two portions dictates: 1) movement of the other of the at least two portions while the one of the at least two portions remains at its existing location on the body surface and 2) subsequent repositioning of the one of the at least two portions while the other of the at least two portions remains in place, such that the respective at least one reference features of the at last two portions abut at a new location and the closed boundary delineates a different segment of the body surface.

22. The locator device of claim 21, wherein the locator device is configured such that abutting the respective at least one reference features to delineate the different segment of the body surface requires one or both of the at least two portions to turn around, flip over or upside down, or rotate.

23. A locator device comprising:
a first portion; and
a second portion operatively connected to, and at least partially detachable from, the first portion,
wherein the first and the second portions have at least one reference feature and, when the at least one reference feature of the first portion abuts the at least one reference feature of the second portion, the first and the second portions form a closed boundary with a central opening, the closed boundary delineating a segment of a body surface on which a procedure is performed; and
wherein the locator device is sized and configured to allow respective the at least one reference features to abut each other even after the first portion and the second portion has been detached from each other and one of the first portion or the second portion has been repositioned on the body surface while the other portion remains in place.

24. The locator device of claim 23, wherein one of the first portion or the second portion, or both comprises a free end when the closed boundary delineates the segment of the body surface.

25. The locator device of claim 23, wherein the central opening is shaped as a square, rectangle or other multi-side opening, and wherein a plurality of fiducial markers is disposed along one or more sides of the opening.

26. The locator device of claim 23, wherein repositioning of the first or the second portions comprises rotating or turning around, or flipping over or upside down.

27. The locator device of claim 26, wherein repositioning comprises turning around 180 degrees and the locator device has dimensions to allow each subsequent delineated segment of the body surface to be immediately adjacent a previous delineated segment of the body surface.

28. The locator device of claim 23, wherein the locator device is dimensioned and configured to allow the closed boundary delineate a different segment of the body surface after each of the first portion and the second portion has been repositioned once while the other portion remained in place and while providing for the abutment of the respective reference features with each repositioning.

* * * * *